United States Patent [19]

Watanabe

[11] Patent Number: 4,747,394

[45] Date of Patent: May 31, 1988

[54] SPINAL RETRACTOR

[75] Inventor: Robert S. Watanabe, Los Angeles, Calif.

[73] Assignee: Watanabe Orthopedic Systems, Inc., Los Angeles, Calif.

[21] Appl. No.: 916,943

[22] Filed: Oct. 8, 1986

[51] Int. Cl.$^4$ ............................................. A61B 17/02
[52] U.S. Cl. ........................................ 128/20; 128/17
[58] Field of Search ...................... 128/20, 14, 17, 345, 128/346; 74/422; 269/227, 202; 254/95, 96, 97, DIG. 6

[56] References Cited

U.S. PATENT DOCUMENTS

| 909,364 | 1/1909 | Carlson | 254/97 |
| 909,469 | 1/1909 | Solberg | 269/227 |
| 968,312 | 8/1910 | Bacon | 254/97 |
| 2,450,194 | 9/1948 | Glaser | 128/20 |
| 3,196,865 | 7/1965 | Rose | 128/20 |
| 4,156,424 | 5/1979 | Burgim | 128/20 |
| 4,316,470 | 2/1982 | Braun et al. | 128/346 |
| 4,627,421 | 12/1986 | Symbas et al. | 128/20 |

FOREIGN PATENT DOCUMENTS

| 625978 | 8/1927 | France | 128/20 |
| 1081863 | 12/1954 | France | 128/20 |

OTHER PUBLICATIONS

Peterson, W. C. "Journal of Bone & Joint Surgery"; vol. 36A; (advertisement) Jan. 1954; pp. 24 & 39.
"Journal of Bone & Joint Surgery"; Jan. 1951-An Improved Spine Retractor; Frantz, Charles.
"U.S. Armed Forces Medical Journal"; vol. II, No. 11; Nov. 1957-A Versatile Spinal Retractor; Batch, J.

Primary Examiner—Richard C. Pinkham
Assistant Examiner—Mark S. Graham
Attorney, Agent, or Firm—Keith D. Beecher

[57] ABSTRACT

A spinal retractor for use in lumbar or dorsal laminectomies or spinal fusions, and for microscopic lumbar laminectomies, which comprises a pair of parallel arms and a corresponding pair of toothed blades which are slidably received on the arms, the blades being forced apart from one another by the arms under the control of a rack and pinion mechanism. The blades are constructed so that their teeth and configuration serve to hold the lumbar musculature when they are forced apart and adequately to expose the facets, and the blades are also configured so that they will not slip out of the wound as they are spread apart by the retractor arms.

2 Claims, 3 Drawing Sheets

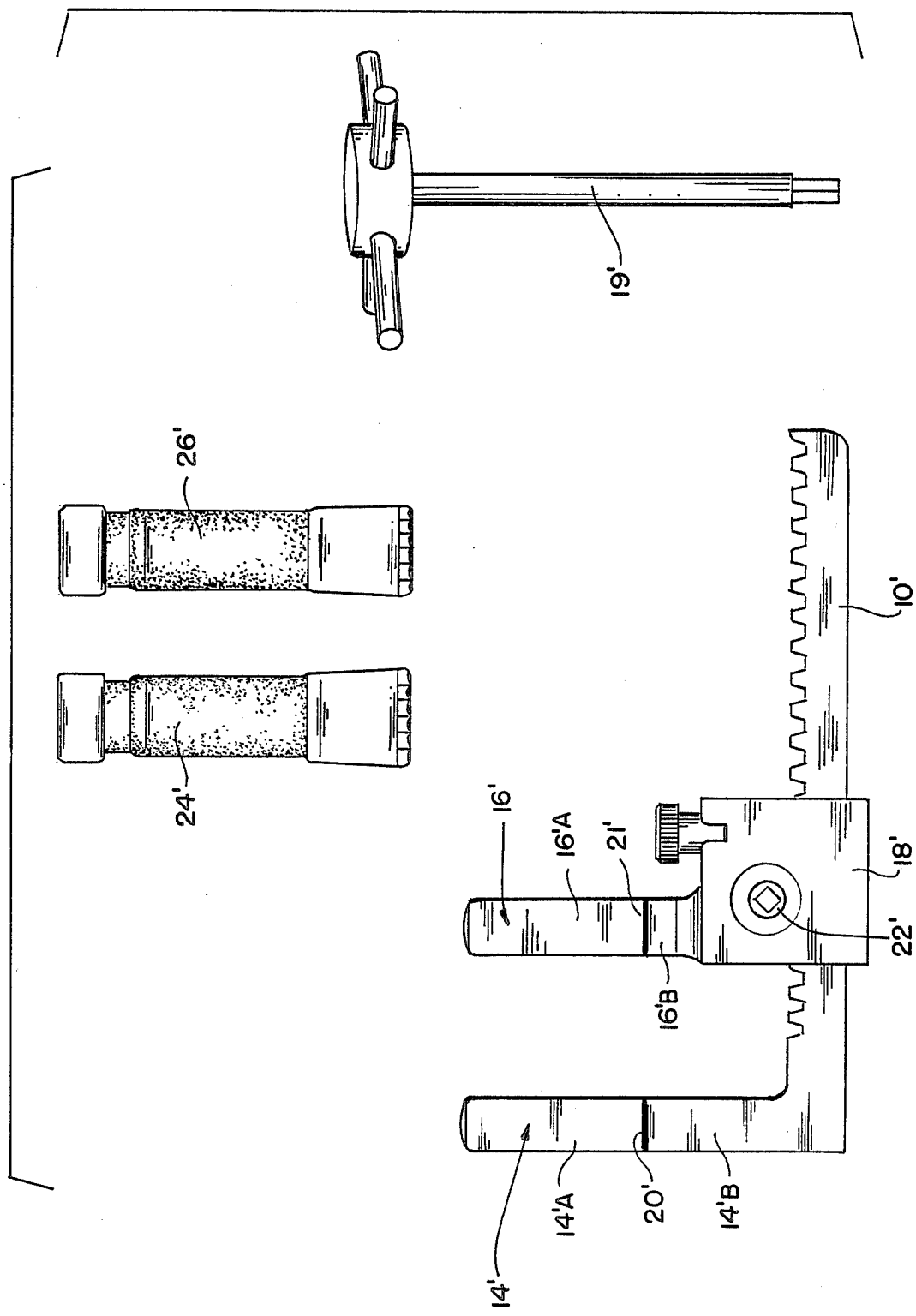

SPINAL RETRACTOR

BACKGROUND OF THE INVENTION

The spinal retractor of the invention is intended for surgical use for lumbar or dorsal laminectomies, or for spinal fusions, as mentioned above. Unlike most prior art lumbar spine retractors, the retractor of the invention is constructed so that its toothed blades do not have a tendency to slip out of the wound as the blades are spread apart. The blades are slidably received on the retractor arms, and they may be replaced by other different size blades, if so desired, for different size patients. As also mentioned, the configuration of the blades is such that the teeth serve to hold the lumbar muscles out of the way, to decrease the ischema and minimize necrosis of these muscles, and adequately to expose the facets.

In a first embodiment of the invention, a double rack is provided to allow for the creation of a significantly large blade spreading force as a pinion handle is turned. Moreover, the rack bars in that embodiment have no tendency to bow as the blades are spread apart.

In a second embodiment which is intended particularly for use in conjunction with microscopic lumbar laminectomy procedures, the blade configuration is similar to that of the first embodiment, but on a smaller scale. A single rack is used because the forces required are not as great as is the case in the intended field of use of the first embodiment.

In both embodiments the retractor arms are preferably hinged to allow for lordosis compensation. Also, the pinion handle is removable to provide a flat surface to assure that there are no impediments to the free movements of the surgeon's hands during the surgical procedure.

In the use of the retractor of both embodiments, the blades are first placed in the wound and set in the muscle above the facets. Once the blades are in the proper position, the retractor arms are inserted into the blades, and the retractor is operated so that the wound may be spread apart by the blades. This procedure allows for the precise placement of the retractor blades above the area of the facets, and it provides for better visualization of the spine.

As mentioned above, the lumbar retractor of the second embodiment is constructed particularly for microscopic procedures. When combined with a surgical microscope, the lumbar retractor of the second embodiment allows for superior visualization of the spinal structure through a small incision.

The retractors of both embodiments are usually provided with a set of variable depth blades for patients of different sizes. In both embodiments, the retractor blades have a sharp teeth design which hold the muscles and prevent the slipping upwardly of the blades to obviate any tendency for the blades to slip out of the wound. The blades are angled to fit the contour of the lumbar muscles and decrease the likelihood of blood circulation problems. Also, the construction is such that there is no tendency for the blades to rotate when the retractor is opened.

BRIEF DESCRIPTION OF THE DRAWINGS

FIG. 3 is a detached view of a microscopic lumbar laminectomy retractor, which is a miniature version of the retractor of FIGS. 1 and 2.

DETAILED DESCRIPTION OF THE ILLUSTRATED EMBODIMENTS

Figure 1:
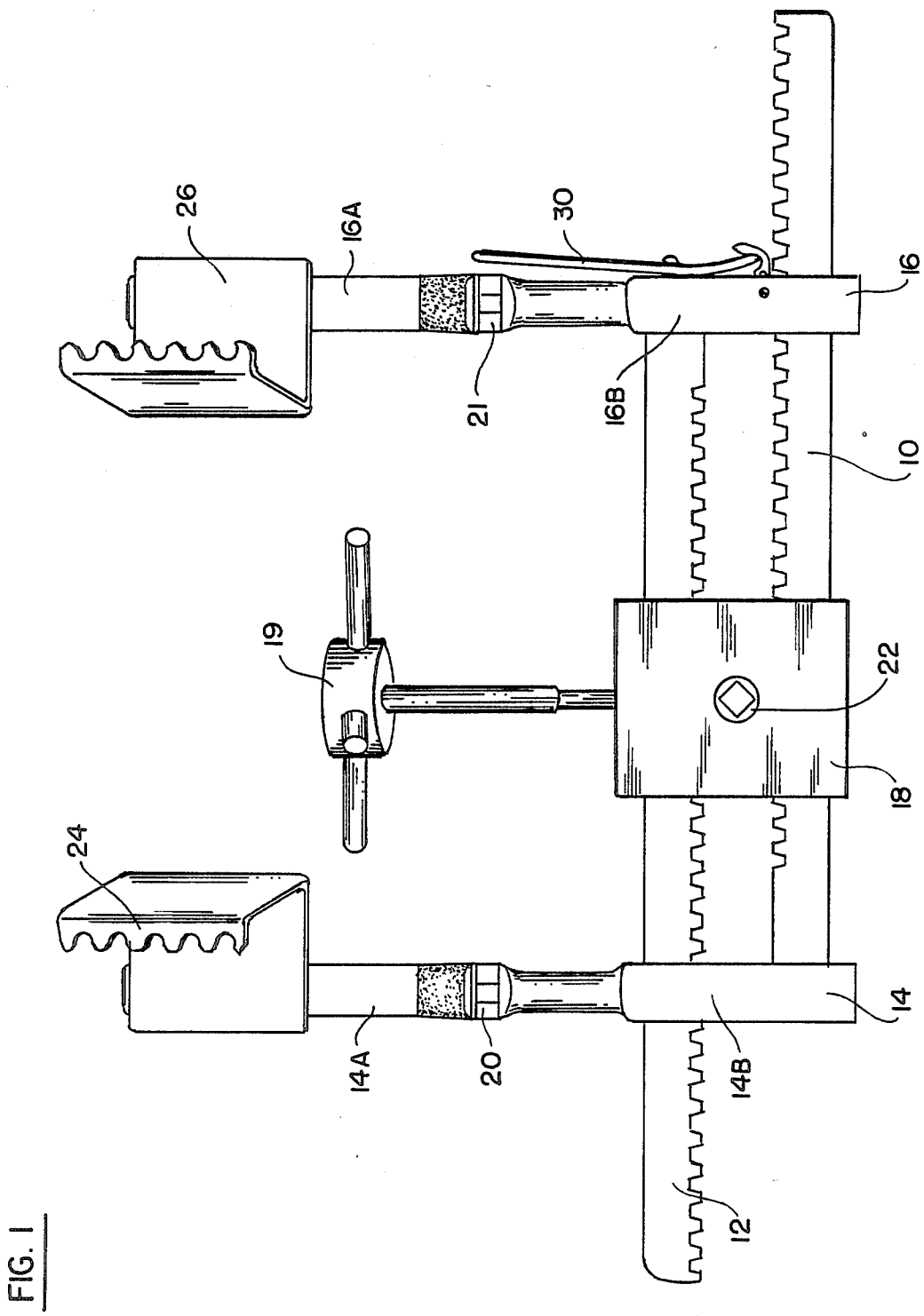
FIG. 1 is a plan view of the retractor of the first embodiment, showing the retractor with a double rack which controls a pair of hinged retractor arms with two blades slidably received on the respective arms.
Figure 2:
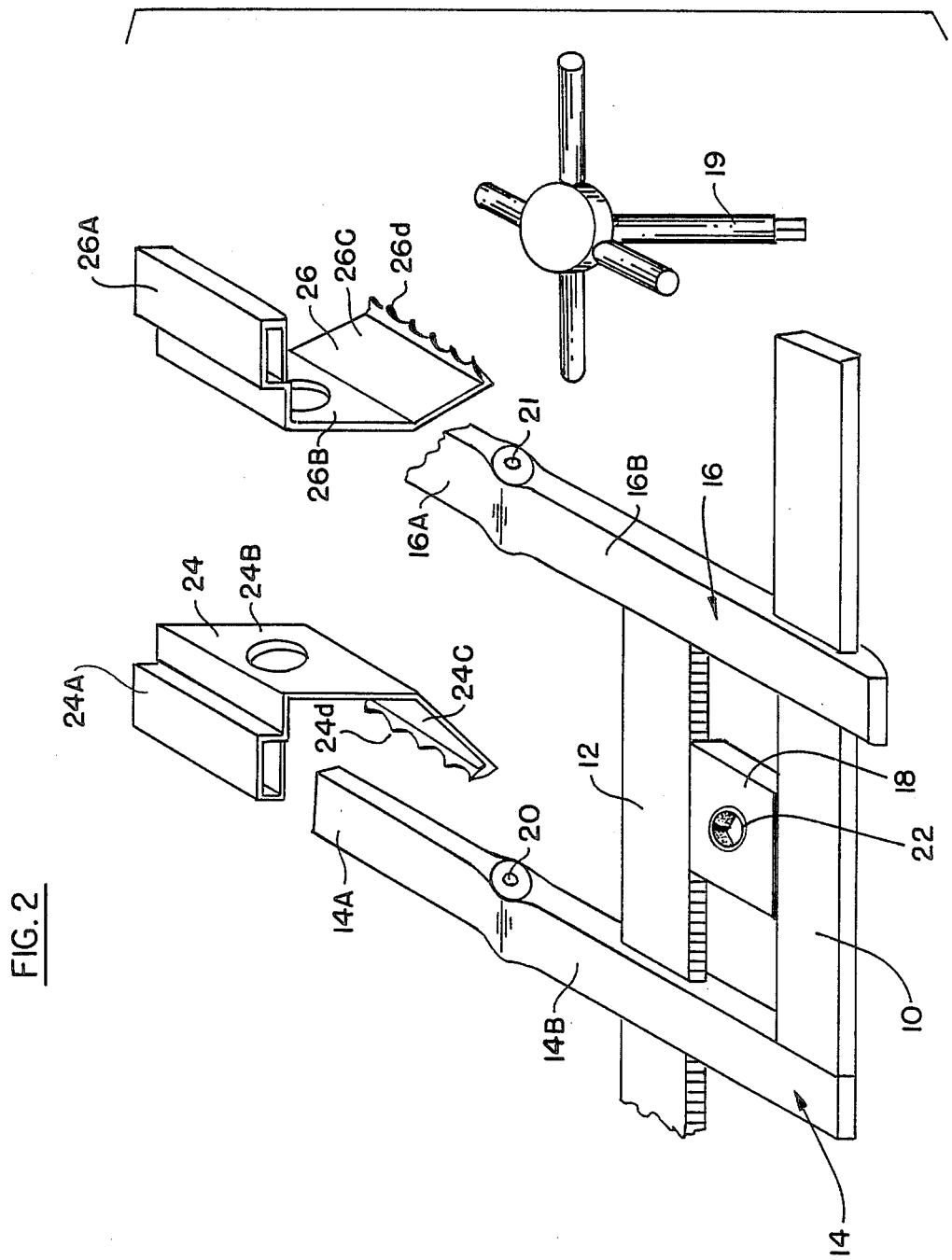
FIG. 2 is a perspective detached view of the retractor assembly of FIG. 1.

The retractor of the embodiment of FIGS. 1 and 2 includes a pair of toothed racks 10 and 12 which extend parallel to one another, with the rack 10 being fastened to a first retractor arm 14 and extending slidably through a second retractor arm 16, and with the rack 12 being fastened to retractor arm 16 and slidably passing through retractor arm 14. The racks 10 and 12 are engaged by a pinion mounted in a casing 18, and which is turned by a handle 19 when the handle is placed in a socket 22 in the pinion.

As the pinion is turned by handle 19, the arms 14 and are caused to move either toward one another or away from one another while maintaining a spaced and parallel relationship.

The arm 14 has a section 14A and a section 14B hinged to one another by a hinge 20, and the arm 16 has a section 16A and a section 16B hinged to one another by a hinge 21.

A pair of blades 24 and 26 are slidably received by Sections 14A, 16A of the respective arms 14 and 16, and may be replaced by other of different sizes, for patients of different sizes.

As best shown in FIG. 2, blade 24 is provided with a bushing section 24A having a rectangular cross-section, and which is received on section 14A of retractor arm 14 in a slidable relationship.

Likewise, blade 26 is provided with a bushing section 26A which is slidably received on section 16A of the retractor arm 16. Bushing 26A also has a rectangular cross-section.

Accordingly, due to the fact that bushings 24A and 26A each has a rectangular cross-section, and each is received in sliding relationship on the respective sections 14A and 16A of arms 14 and 16, there is no tendency for the blades to rotate as the pinion in casing 18 is turned to spread the blades apart.

In addition, blade 24 includes an intermediate planar section 24B which extends perpendicularly down from the plane of the retractor arms 14 and 16, and blade 26 has an intermediate planar section 26B which, likewise, extends down from the plane of the retractor arms 14 and 16.

Blade 24 has a lower planar section 24C which is inclined to section 24B, and which is terminated in a set of teeth 24D which extend upwardly from the edge of the section 24C. Blade 26 has a corresponding lower planar section 26C which is provided with teeth 26D.

As mentioned above, the sharp teeth 24D and 26D of the retractor blades serve to hold the muscles and prevent slipping upwardly of the retractor blades during the surgical procedure. Moreover, the sections 24B and 24C of blade 24 and sections 26B and 26C of blade 26 are angled to fit the contour of the lumbar muscles and decrease the chance of blood circulation problems to the lumbar muscles. The blades are also adjustable along the respective retractor arms 14 and 16 due to the fact that they are not fixed to the arms but slidably engage the arms. Moreover, the specific blades may be removed and replaced by other blades depending on the size of the patient.

As explained above, in the use of the retractor assembly, the blades 24 and 26 are first placed into the wound in the proper position, and then the sections 14A and 16A of the retractor arms are fitted into the bushing sections 24A and 26A. As also explained, the retractor arms 14 and 16 are hinged by hinges 20 and 21 to allow for lordosis compensation. As illustrated, handle 19 is removable to provide for freedom of movement of the surgeon's hands during the surgical procedure.

The microscopic lumbar laminectomy retractor shown in FIG. 3 is similar to the retractor shown in FIG. 1, and like components have been designated by the same numbers primed.

As mentioned above, the retractor of FIG. 3 is constructed particularly for microscopic procedures, and it provides excellent visualization through a small incision. Like the retractor of FIGS. 1 and 2, the retractor of FIG. 3 may be provided with a number of different size blades 24', 26' for different size patients. The blade configuration is similar to the configuration of the blades of the first embodiment, but on a smaller scale.

As illustrated, a single rack 10' is used because the forces encountered by the retractor of FIG. 3 are less than those encountered in the normal field of use of the retractor of FIGS. 1 and 2.

The invention provides, therefore, an improved laminectomy retractor which is simple in its concept, and which is relatively easy to use. As explained, the retractor of the present invention is constructed to overcome problems encountered by the prior art laminectomy retractors which have a tendency to slip out of the wound when the retractor arms are spread apart. Another important advantage of the retractor of the invention is the configuration of the toothed blades which serve to hold the muscles when the blades are forced apart adequately to expose the facets, and to provide superior visualization of the spinal structures.

Although particular embodiments of the invention have been shown and described, modifications may be made. It is intended in the claims to cover all modifications which come within the true spirit and scope of the invention.

I claim:

1. A laminectomy retractor comprising: a pair of arms each having a rectangular cross-section; a rack and pinion mechanism attached to said arms for holding said arms in spaced and parallel relationship and for displacing said arms away from one another; and a pair of blades slidably and removably mounted on respective ones of said arms to be inserted into a patient's spinal wound during a surgical procedure to space the sides of the wound apart to provide visualization of the spinal structure and to hold the sides of the wound in spaced-apart position, each of said blades including a bushing having a rectangular cross-section to be slidably received on the respective arms, so that the blades are held on the respective arms in a non-rotatable relationship so that there is no tendency for the blades to slip out of the wound as the retractor arms are spread apart, and each of said blades being configured to include a first rectangular section integral with said bushing and extending downwardly from the plane of the retractor, and a second rectangular section integral with the lower edge of said first section and inclined outwardly with respect thereto, and a series of outwardly extending teeth formed on the lower edge of said second rectangular section and extending upwardly therefrom, the teeth and configuration of the blades serving to hold the lumbar muscles when the blades are forced apart and adequately expose the facets; said a rack and pinion mechanism including a pair of racks positioned perpendicular to said arms and spaced and parallel to one another to be engaged by said pinion, the racks being attached to respective ones of said arms and slidably passing through the other ones of said arms, and said pinion being rotatably mounted between said racks and engaging said racks.

2. The laminectomy retractor defined in claim 1, in which each of said arms is formed of two sections hinged to one another to permit lordosis compensation.

* * * * *